(12) United States Patent
Morman et al.

(10) Patent No.: US 8,328,780 B2
(45) Date of Patent: Dec. 11, 2012

(54) ABSORBENT ARTICLE WITH ELASTOMERIC BORDERED MATERIAL

(75) Inventors: Michael T. Morman, Alpharetta, GA (US); Patricia H. Calhoun, Alpharetta, GA (US); James M. Carr, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2125 days.

(21) Appl. No.: 10/301,664

(22) Filed: Nov. 21, 2002

(65) Prior Publication Data

US 2004/0102755 A1    May 27, 2004

(51) Int. Cl.
*A61F 13/15* (2006.01)
*A61F 13/20* (2006.01)

(52) U.S. Cl. ............... 604/385.01; 604/385.24

(58) Field of Classification Search .. 604/385.22–385.3, 604/396, 392–394, 397, 385.201
See application file for complete search history.

(56) References Cited

U.S. PATENT DOCUMENTS

| | | | |
|---|---|---|---|
| 3,999,547 A | 12/1976 | Hernandez | |
| 4,100,324 A | 7/1978 | Anderson et al. | |
| 4,209,563 A | 6/1980 | Sisson | |
| 4,606,964 A | 8/1986 | Wideman | |
| 4,610,681 A | 9/1986 | Strohbeen et al. | |
| 4,641,381 A | 2/1987 | Heran et al. | |
| 4,655,760 A | 4/1987 | Morman et al. | |
| 4,657,802 A | 4/1987 | Morman | |
| 4,663,220 A | 5/1987 | Wisneski et al. | |
| 4,695,278 A | 9/1987 | Lawson | |
| 4,704,116 A | 11/1987 | Enloe | |
| 4,720,415 A | 1/1988 | Vander Wielen et al. | |
| 4,741,949 A | 5/1988 | Morman et al. | |
| 4,743,241 A | 5/1988 | Igaue et al. | |
| 4,747,846 A | 5/1988 | Roland et al. | |
| 4,781,966 A | 11/1988 | Taylor | |
| 4,789,699 A | 12/1988 | Kieffer et al. | |
| 4,938,753 A | 7/1990 | Van Gompel et al. | |
| 4,940,464 A | 7/1990 | Van Gompel et al. | |
| 4,965,122 A | 10/1990 | Morman | |
| 4,981,747 A | 1/1991 | Morman | |

(Continued)

FOREIGN PATENT DOCUMENTS

EP    0217032 B1    2/1992

(Continued)

OTHER PUBLICATIONS

U.S. Appl. No. 10/301,880, filed November 21, 2002.

(Continued)

*Primary Examiner* — Susan Su
(74) *Attorney, Agent, or Firm* — Dority & Manning, P.A.

(57) ABSTRACT

An absorbent article incorporates a material having a base layer of a generally fluid permeable material and at least two strips or regions of elastomeric material attached to the base layer material with a space therebetween such that a center region of the base layer material is bordered on at least two sides by composite regions of the elastomeric materials and the base layer material. The center region of base layer material remains generally non-elastic and the composite regions are stretchable in at least a first direction as a result of tensioning and necking-in the base layer material prior to attaching the elastomeric materials. The material may be incorporated as a bodyside liner in the absorbent article.

43 Claims, 8 Drawing Sheets

U.S. PATENT DOCUMENTS

| | | | |
|---|---|---|---|
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,224,405 A | 7/1993 | Pohjola |
| 5,226,992 A | 7/1993 | Morman |
| 5,284,703 A | 2/1994 | Everhart et al. |
| 5,336,545 A | 8/1994 | Morman |
| 5,350,624 A | 9/1994 | Georger et al. |
| 5,368,584 A | 11/1994 | Clear et al. |
| 5,486,166 A | 1/1996 | Bishop et al. |
| 5,490,846 A | 2/1996 | Ellis et al. |
| 5,500,063 A | 3/1996 | Jessup |
| 5,545,158 A | 8/1996 | Jessup |
| 5,601,547 A | 2/1997 | Kato et al. |
| 5,620,431 A | 4/1997 | LeMahieu et al. |
| 5,680,653 A | 10/1997 | Mathis et al. |
| 5,683,752 A | 11/1997 | Popp et al. |
| 5,711,832 A | 1/1998 | Glaug et al. |
| 5,820,973 A | 10/1998 | Dodge, II et al. |
| 5,846,232 A | 12/1998 | Serbiak et al. |
| 5,851,204 A | 12/1998 | Mizutani |
| 5,910,224 A | 6/1999 | Morman |
| 5,947,947 A | 9/1999 | Tanzer et al. |
| 6,020,535 A | 2/2000 | Blenke et al. |
| 6,168,585 B1 | 1/2001 | Cesco-Cancian |
| 6,231,557 B1 | 5/2001 | Krautkramer et al. |
| 6,336,921 B1 | 1/2002 | Kato et al. |
| 6,358,350 B1 | 3/2002 | Glaug et al. |
| 6,362,389 B1 | 3/2002 | McDowell et al. |
| 6,506,329 B1 | 1/2003 | Curro et al. |
| 6,843,872 B2 * | 1/2005 | Morman ................ 156/163 |
| 2002/0086602 A1 | 7/2002 | Friderich et al. |
| 2003/0208171 A1 | 11/2003 | Zehner et al. |

FOREIGN PATENT DOCUMENTS

| | | |
|---|---|---|
| EP | 0547497 | 6/1993 |
| EP | 0638302 | 2/1995 |
| EP | 0638302 A1 | 2/1995 |
| EP | 1080708 A2 | 3/2001 |
| WO | 9519258 | 7/1995 |
| WO | 9620680 | 7/1996 |
| WO | 9816677 | 4/1998 |
| WO | WO 9933426 | 7/1999 |
| WO | 0019950 | 4/2000 |
| WO | 0035395 | 6/2000 |
| WO | 0188245 A2 | 11/2001 |
| WO | 0228334 | 4/2002 |
| WO | 02069867 | 9/2002 |
| WO | 2004 047702 | 6/2004 |

OTHER PUBLICATIONS

Patent Abstract of Japan No. 2001212174, Published Aug. 7, 2001.
U.S. Appl. No. 10/730,493, filed Dec. 8, 2003.
U.S. Appl. No. 10/730,364, filed Dec. 8, 2003.
EPO Search Report, May 4, 2004.
PCT Written Opinion, Oct. 18, 2004.
International Preliminary Examination Report, Jan. 14, 2005.

* cited by examiner

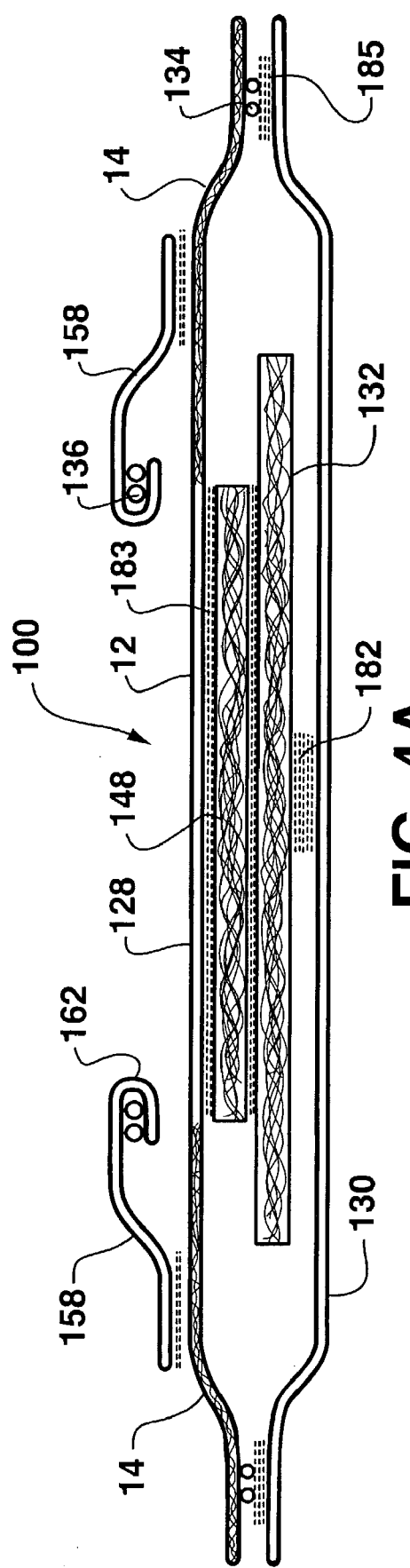
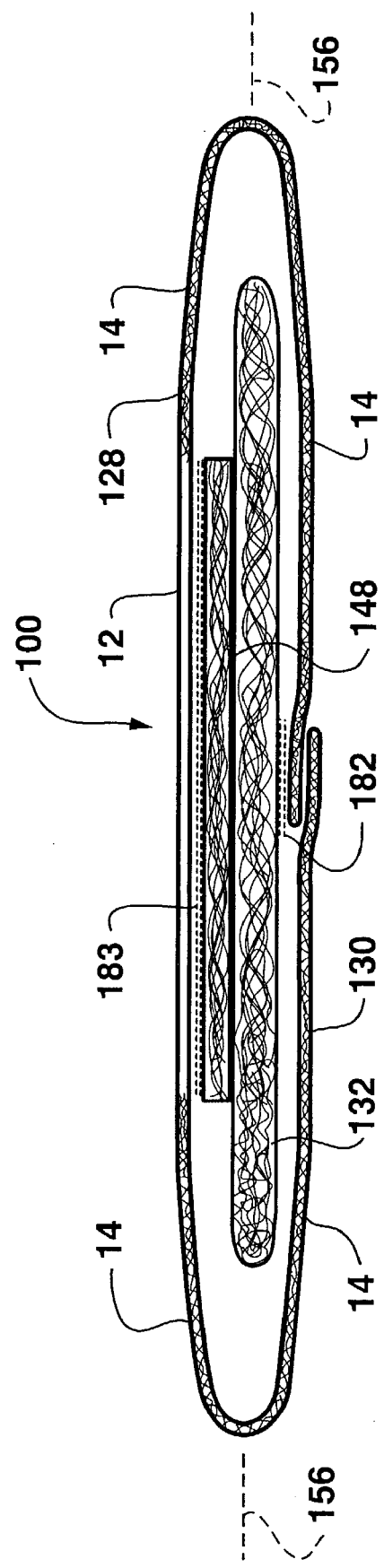

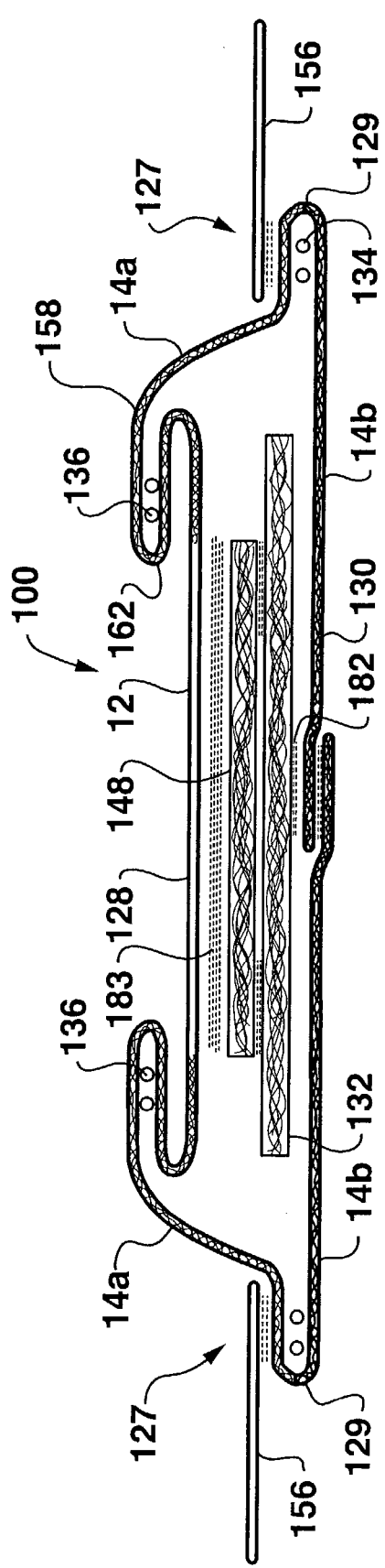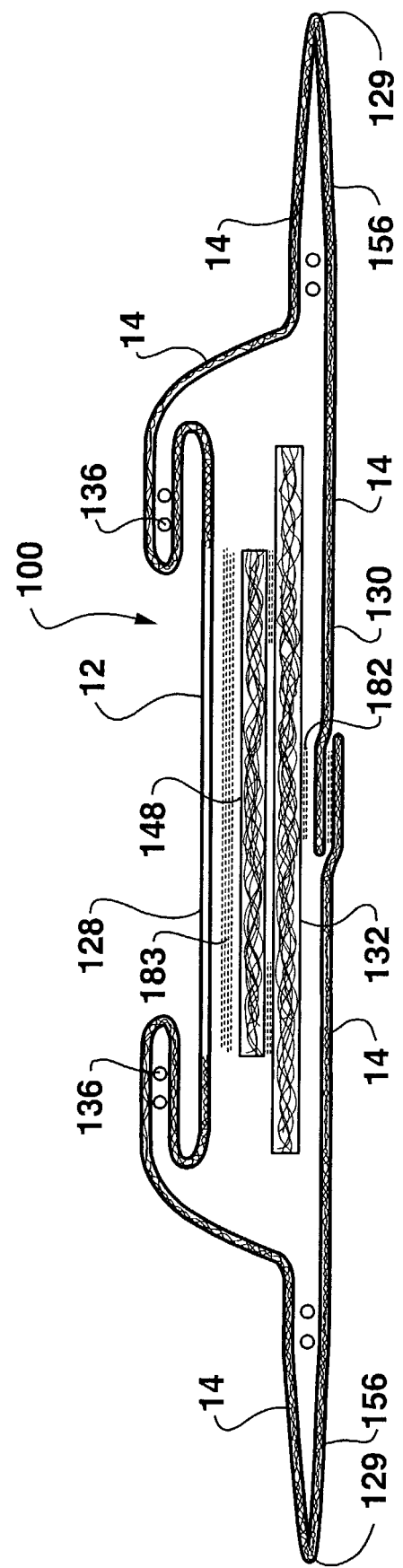

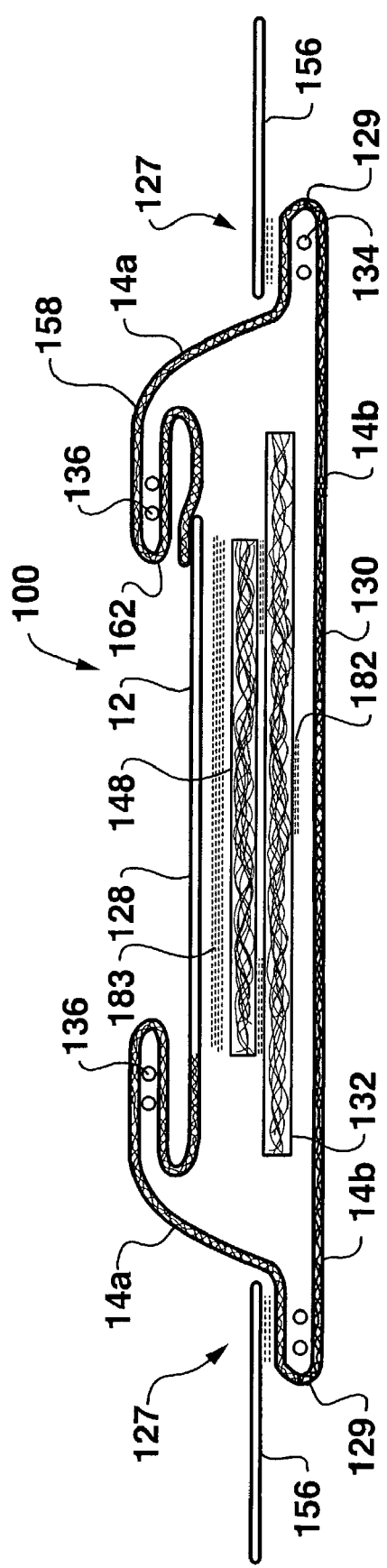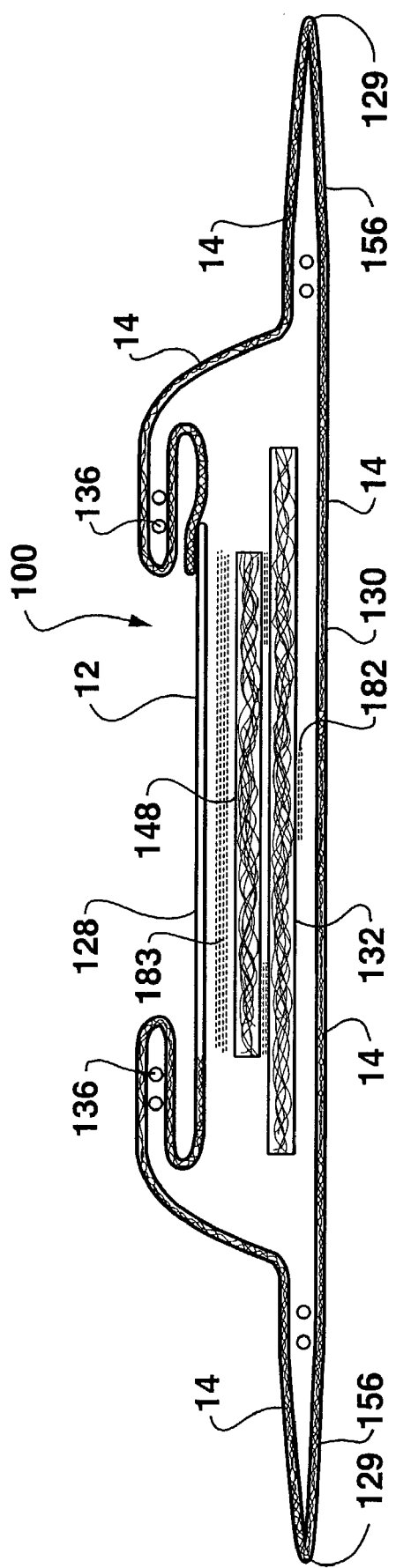

ABSORBENT ARTICLE WITH ELASTOMERIC BORDERED MATERIAL

TECHNICAL FIELD OF THE INVENTION

The present invention relates generally to the field of absorbent articles and garments, such as children's training pants, disposable diapers, incontinence articles, and the like, and more particularly to an improved product design utilizing an improved material for use in such articles.

BACKGROUND

Many types of disposable absorbent articles such as disposable diapers, training pants, feminine care articles, incontinence articles, and the like, utilize a design incorporating an absorbent pad, a surge layer, a bodyside liner material, containment flaps, a liquid impervious barrier layer, and side portions that can be brought together to close the article around the wearer's body. Often, various portions of these product designs are elasticized in some way to provide a comfortable fit and a gasket function to help reduce leakage. The liquid transfer and absorbency capabilities of the absorbent system depend, in large part, on maintaining the structural integrity and characteristics of the component parts. The structure (e.g., bulk weight, density, capillary structure) of the underlying absorbent material is tailored for particular flow rates and total absorbency depending on the type of absorbent article.

The absorbency, fit, and leakage protection properties of these products are determined in large part by the capillary structure of the components making up the absorbent system, and the elastic properties of various materials used in the total construction. The capillary structure of the various absorbent components is specifically designed and it is desirable to maintain the structure during the entire time the product is being used. Currently, many types of products utilize a piecemeal approach to provide elastic properties by attaching elastic or extensible materials to other components that have little or no elastic properties. The overall effect is to provide stretch for gasketing, fit, and comfort in some portions of the product, while keeping the absorbent components in a relatively non-stretched state to maintain the capillary structure for good absorbency. With products where the entire chassis may be stretchable, the stretching of the liner and rest of the absorbent system causes the capillary structure and fluid handling properties to also change. The capillary structure would change if the absorbent components are stretched. For example, if a necked material with a given fiber and capillary structure is used as a bodyside liner material and is stretched in a direction, the fibers are forced to move and/or rotate to accommodate the stretch. This movement and/or rotation of the fibers changes the capillary structure of the necked nonwoven material. If the necked, non-stretched nonwoven had an ideal capillary structure before stretching, the stretched material will no longer have that ideal structure. In general, any changes in the dimensions of the material in width, length, or thickness will change the capillary structure.

A product design that includes elastic materials attached to non-elastic, non-extensible materials often requires a process that brings the various materials together in a rather complicated fashion, and may attach the components together in ways that 'tie-up', or negate, the functionality of the elastic materials in these areas of attachment. Other attachment means may reduce the functionality of the elastic components, or require more expensive components to overcome the effect of attachment to the article.

It has been found that overall extendable or elastomeric absorbent products are highly desirable for fit, comfort, and containment. It can be seen that a problem may occur in that for optimum absorbency, the product should not extend, but for fit, comfort, and containment, it should extend without the complications that arise from attaching multiple elastic and non-extensible components together. The present invention resolves this dilemma.

SUMMARY OF THE INVENTION

Objects and advantages of the invention will be set forth in part in the following description, or may be obvious from the description, or may be learned through practice of the invention.

In general, the present invention provides a product design particularly suited for use as an absorbent article, such as disposable diapers, child's training pants, incontinence articles, feminine care products, diaper pants, disposable swim pants, and the like. The product design makes use of a single material that can comprise many portions of such absorbent articles, such as the bodyside liner material, the containment flaps, the side portions and the outer barrier or cover layer. The invention also includes methods for making the material. The invention also greatly reduces the number of different materials required to construct the article, which simplifies the process to produce it, and greatly reduces the number of attachment points, which can hinder the overall performance of the elastic portions of the product.

A method is provided according to the invention for producing a material having at least one liquid permeable region bordered at least partially by elastomeric or extendable composite regions. Although not limited to such use, the resulting material is particularly well suited to provide multiple functions in disposable absorbent articles, such as a bodyside liner material, a containment flap material, a stretchable side portion, and a cloth-like liquid impermeable barrier or cover material. The method includes providing a layer of material, such as a spunbond nonwoven web, and applying a tensioning force to the material in a first direction to neck it in a second direction. The tensioning force may be applied, for example, in the machine direction. At least one strip of an elastomeric material, such as an elastic film, elastomeric nonwoven web, combination or composite of different or the same elastomeric materials, etc., is superimposed along a side of the necked material, for example along a lateral side. In a particular embodiment, an elastomeric strip is superimposed along each lateral side. The elastomeric strips have a width that is less than the width of the necked material such that a region or strip of the necked material is defined between the elastomeric material strips. For example, the elastomeric material strips may each have a width of about one-third of the width of the necked material. The elastic material strips are attached to the necked material by any suitable method, for example by bonding or adhering the materials in a laminating process.

Upon releasing the tensioning force, the portion of the necked material that has no attached elastic material can relax to generally its pre-necked width and is bordered on at least one side, and optionally two sides, by a laminate composite structure that is stretchable, for example in the cross direction. As a result, one of ordinary skill in the art can readily appreciate that the center region of the necked material, that has returned to generally its pre-necked width, is inherently less extensible than the composite regions in a lateral direction of the necked material within the composite regions.

The center region or strip of material that has not been laminated with elastic material may be liquid permeable and have other desired properties of conventional bodyside liner materials. An embodiment of the material may thus serve as a bodyside liner wherein the center region or strip of material that has not been laminated with elastic material overlies an absorbent body structure in an absorbent article. This center region may be adhered to the underlying absorbent body structure to ensure that its capillary structure does not change upon stressing (stretching) the elastomeric portions. The side strips of composite material may extend out to serve as elastomeric side portions and provide the absorbent article chassis with desired degrees of stretch without compromising the structural integrity or characteristics of the liquid permeable center region or underlying absorbent body structure. The side panels and an elastic outer cover may extend independently from the entire structure, in which case the absorbent structure need not extend and have its liquid handling properties change when the chassis is stretched.

The elastic composite side portions of the material may also be folded under the absorbent body structure and thus serve as the outer cover for the article. Separate side portions may be attached where the material is folded under to complete the article chassis. A third embodiment includes using a material wherein the elastic composite portions extend out to serve as elastic side portions and also fold under to serve as the barrier outer cover.

The elastomeric "strips" may be a single layer of material, such as an elastic film, or a composite of multiple materials, such as side-by-side layers of the same or different materials. The strips may have varying elastomeric properties. For example, a single elastomeric material may be used having different bond densities or properties in different areas of the laminates. Layers of the same or different elastomeric material may overlie each other in laminate regions. Each strip may be the same as the other strip, or the strips may be of different elastomeric materials. Numerous combinations of elastomeric materials are within the scope and spirit of the invention.

Similarly, the non-elastic base material may be a single layer of material, such as a nonwoven web, or a composite of multiple layers of the same or different materials.

In one particular embodiment, the elastomeric materials in an untensioned state are attached to the lateral sides of the necked material such that the resulting laminate side portions of the material are stretchable in the transverse direction. In an alternate embodiment, the elastomeric material strips are attached to the lateral sides of the necked material in a tensioned state such that upon releasing the tensioning force, the non-elastic portion of the material not attached to elastomeric material is gathered or creped in the machine direction and thus extensible in the longitudinal direction, and the side laminate portions are stretchable in the transverse and longitudinal directions. Alternatively, the non-elastic base material may be inherently extensible in the machine direction. For example, the material may be creped or gathered prior to attaching the elastic material strips. The gathering of the necked material should not significantly change its capillary structure. Ideally the capillary structure would not be changed at all.

In still another embodiment, the elastomeric material strips are attached to the opposite longitudinal ends of the necked base material. The resulting material has longitudinally separated elastomeric regions that are transversely stretchable separated by and bordering a center cross direction region of the base material.

It may be desired to border the base material with elastic on all sides, such as in a "picture frame" configuration. For example, the base material may be tensioned in the machine direction (necked), and the elastomeric material strips joined to the opposite lateral sides and longitudinal ends of the base material. The resulting material has lateral and longitudinal elastomeric regions framing a region of necked material.

The invention encompasses any manner of absorbent article incorporating the novel material as described herein. For example, any configuration of a disposable diaper, child's training pant, incontinence article, feminine care product, and the like, may incorporate the material. In an embodiment of a disposable diaper or training pant, the material may be provided as the bodyside liner wherein the liquid permeable center strip or region overlies an absorbent body structure. The elastomeric side strips of the composite material may have a width so as to extend to the lateral sides of the article chassis. A separate outer cover member may be attached to the composite side strips by any conventional technique such that the absorbent body structure is sandwiched between the liner and outer cover member. If the outer cover stretches, the underlying absorbent structure may not be stretched. In this embodiment, separate containment flaps may be attached to the bodyside liner portion of the composite material. Alternatively, the composite elastomeric side strips may be folded in a manner, such as a Z-fold configuration, so as to also define containment flaps. For particular absorbent article configurations, such as a child's training pant, elastomeric side panels may be attached to the lateral sides of the chassis. Upon folding the chassis, the side panels are joined at side seams (permanent or re-fastenable) to form a pant-like structure. This type of configuration is known, for example, from the Huggies® Pull-Ups® disposable training pants from Kimberly-Clark Corporation of Neenah, Wisconsin, USA.

In an alternate absorbent article embodiment, the elastomeric composite side strips have a substantial width and are folded under the absorbent body structure to also define the outer cover member. In this embodiment, the base material and elastomeric material are selected so that the composite side strips will have the desirable characteristics of an outer cover member. As with the previous embodiment, separate containment flaps may be attached to the bodyside liner portion of the composite material. Alternatively, the composite side strips may be folded in a manner, such as a Z-fold configuration, so as to also define containment flaps. As described above, elastomeric side panels may be attached to the chassis and joined at side seams.

With still another embodiment according to the invention, the elastomeric composite side strips have even a greater width and also define the front and back side portions of the chassis, these portions being joined or joinable at side seams to define the article. Separate containment flaps may be attached to the bodyside liner portion of the composite material, or the composite side strips may be folded in a manner, such as a Z-fold configuration, so as to also define containment flaps.

It should be appreciated that the invention also encompasses a material (and articles utilizing such material) wherein only a single lateral or longitudinal side includes the elastomeric composite structure. This single side may be of a sufficient width so as, for example, to fold completely under an absorbent structure and attach to the opposite lateral side of the non-extensible material thereby defining an outer barrier cover. The single side composite may have a width so as to also define containment flaps, elastomeric side panels, and so forth, as described above.

Aspects of the invention will be described below in greater detail with reference to embodiments shown in the figures.

BRIEF DESCRIPTION OF THE FIGURES

FIG. 4A is a schematic cross-sectional view of the article of FIG. 4 taken along the lines indicated.

FIG. 4B is a schematic cross-sectional view of an alternative absorbent article incorporating the composite material of the invention.

FIG. 5 is a schematic cross-sectional view of an alternate embodiment of an absorbent article according to the invention.

FIG. 6 is a schematic cross-sectional view of still another embodiment of an absorbent article according to the invention.

FIG. 8 is a schematic cross-sectional view of an alternate embodiment of an absorbent article according to the invention.

FIG. 9 is a schematic cross-sectional view of still another embodiment of an absorbent article according to the invention.

DETAILED DESCRIPTION

Figure 1:
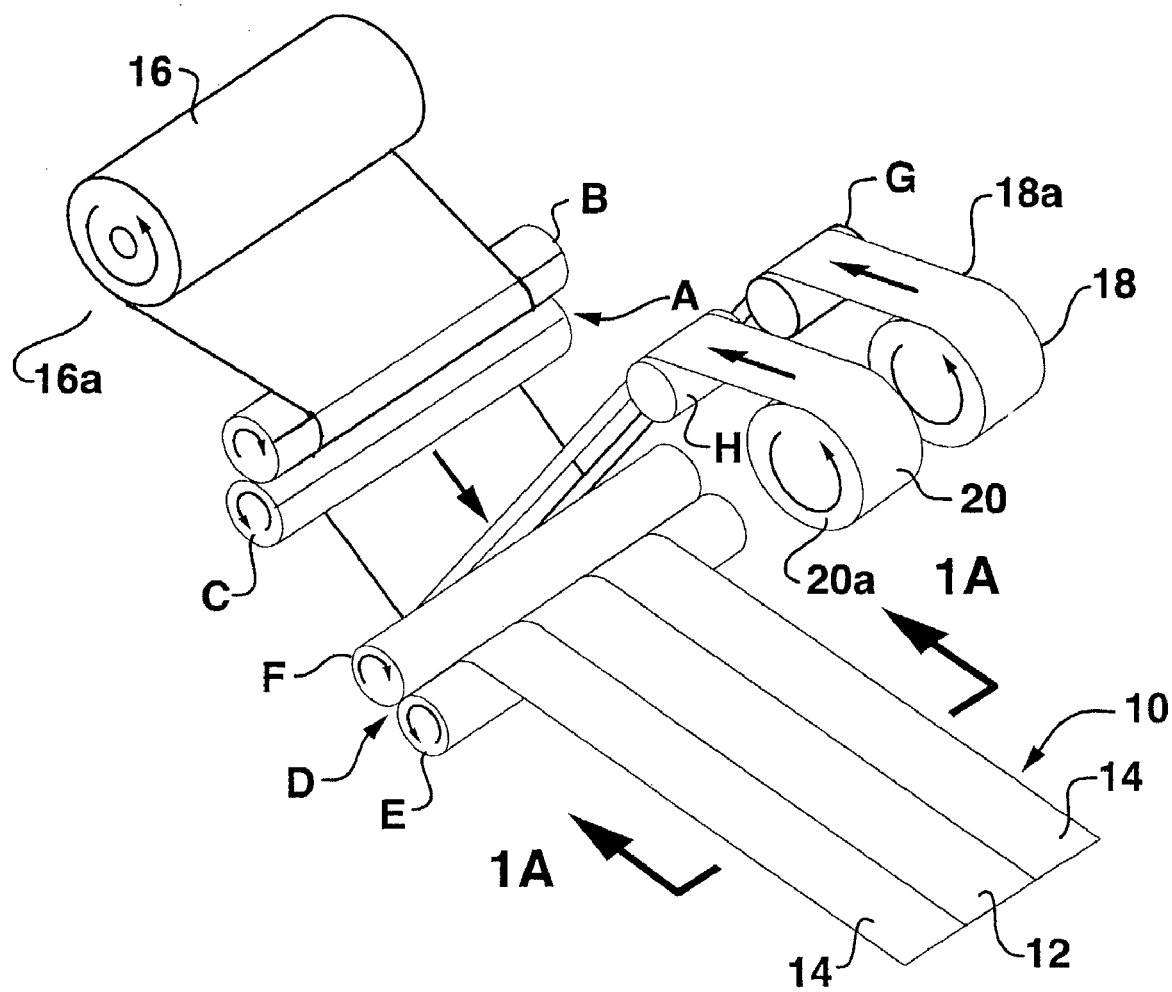
FIG. 1 is a schematic representation of an exemplary process for forming a composite material in accordance with the invention.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Within the context of the present description, the following terms may have the following meanings:

"Machine direction" refers to the length of a fabric or material in the direction in which it is produced or converted, as opposed to "cross direction" or "cross-machine direction" which refers to the width of a fabric in a direction generally perpendicular to the machine direction.

"Attached" and "joined" refers to the bonding, adhering, connecting, and any other method for attaching or joining two elements. Two elements will be considered to be attached or joined together when they are bonded directly to one another or indirectly to one another, such as when each is directly attached to an internediate element.

"Extendable" or "extensible" means that property of a material or composite by virtue of which it stretches or extends in the direction of an applied biasing force by at least about 25% of its relaxed length. An extendable material does not necessarily have recovery properties. For example, an elastomeric material is an extendable material having recovery properties. A meltblown web may be extendable, but not have recovery properties and, thus, be an extensible but non-elastic material.

"Elastomeric," "elastic," and "elasticized" refer to a material or composite which can be elongated by at least 25% of its relaxed length and which will recover, upon release of the applied force, at least 10% of its elongation. It is generally preferred that the elastomeric material or composite be capable of being elongated by at least 100%, more preferably by at least 300%, of its relaxed length and recover at least 50% of its elongation. An elastomeric material is an extendable material having recovery properties.

"Non-extensible" refers to a material that does not stretch or extend by at least about 25% of its relaxed length without fracture upon application of a biasing force. Materials that are extensible or elastomeric are not considered "nonextensible."

"Necked material" refers to any material which has been constricted in at least one dimension by processes such as, for example, drawing.

"Neck-bonded" laminate refers to a composite material having an elastic member that is bonded to a member while the member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Reversibly-necked material" refers to a necked material that has been treated while necked to impart memory to the material so that when force is applied to extend the material to it pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is described in U.S. Pat. Nos. 4,965,122 and 4,981, 747, incorporated herein by reference for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,720,415, 4,789,699, 4781,966, 4,657,802, and 4,655,760, which are incorporated herein by reference in their entirety for all purposes.

"Neck stretch-bonded" laminate refers a laminate made from the combination of a neck-bonded laminate and a stretch-bonded laminate. Examples of necked stretch bonded laminates are disclosed in U.S. Pat. Nos. 5,114,781 and 5,116, 662, which are incorporated herein in their entirety by reference thereto for all purposes. A necked stretch bonded laminate can be stretchable in both the machine and cross-machine directions.

"Nonwoven web" refers a web that has a structure of individual fibers or threads which are interlaid, but not in an identifiable, repeating manner. Nonwoven webs may be formed, for example, by a variety of processes including melt-blowing, spunbonding, and bonded carded web processes.

"Sheet" refers to a layer which may be either a film, a foram, or a nonwoven web.

"Member" when used in the singular can refer to a single element or a plurality of elements.

"Untensioned" as used herein to describe a material web does not mean lacking all tension. In order to handle and process moving webs, some moderate amount of tension is needed to hold the web or material in place. An "untensioned" web or material, as used herein, is under enough tension to process the material, but less than that required to cause substantial deformation of the material.

Various aspects and embodiments of the invention will be described in the context of a material for disposable absorbent articles, such as disposable diapers, children's training pants, incontinence articles, feminine care products, diaper pants, disposable swim pants, and the like. It should be appreciated that this is for illustrative purposes only, and that the invention is not limited to any particular absorbent article, or absorbent articles in general. The material according to the invention may have beneficial uses in any number of applications, such as protective medical clothing, drapes, gowns, and the like.

Referring to FIGS. 1, 1A, 2A, 2B, and 2C a composite material 10 according to the invention and method of making are illustrated. The depicted method is related in certain aspects to the method described in U.S. Pat. No. 5,226,992 for making an elastic neck bonded laminate, and the '992 patent is incorporated herein in its entirety for all purposes.

In one particular process of making the material 10 (FIG. 1), a neckable generally non-extensible material 16 is unwound from a supply roll 16a and travels in the direction illustrated by the arrows. The non-extensible material 16 passes through the nip A of the drive roller arrangement formed by rollers B and C. Embodiments of particular types of neckable non-extensible material 16 are described in detail below.

At least a first sheet of elastomeric material 18, such as an elastic film or meltblown, is unwound from a supply roll 18a in the direction indicated by the arrows. In a particular embodiment, a second sheet of elastomeric material 20, such as an elastic film, is unwound from a supply roll 20a in the direction indicated by the arrows. The sheets 18 and 20 each have a width that is less than that of the non-extensible material 16 after it is necked, for example the sheets 18 and 20 may have a width that is one-third of the width of the sheet 16. As described below, the respective widths of the sheets may be varied according to the final use of the composite material 10. Also, the sheets 18 and 20 may have different widths.

The elastomeric sheets 18 and 20 may be the same type of elastomeric material, such as the same film, or a composite of different materials. Particular embodiments of suitable elastomeric materials are described in detail below.

The elastomeric sheets 18 and 20 are directed by guide rollers G and H through the nip D of the bonder roller arrangement formed by rollers E and F. The sheets 18 and 20 can, but need not necessarily, be registered with the material 16 so as to be disposed on and aligned with respective lateral sides of the material 16, as generally indicated in the figures.

The non-extensible material 16 passes through the nip A of the S-roller arrangement of rollers B and C in a reverse-S path, and then through the pressure nip D of the bonder rollers E and F. Material 16 is necked prior to being attached to elastomeric sheets 18 and 20. For example, as shown in FIG. 1, the material 16 may be necked between the supply roll 16a and rollers B and C of the S-roll arrangement, by controlling the peripheral linear speed of the supply roll 16a to be less than the peripheral linear speed of the rollers B and C. The material 16 is thus tensioned in the machine direction and necked-in in the cross direction between the supply roll and the S-roll arrangement. Alternately, the peripheral linear speed of rollers B and C of the S-roll arrangement may be controlled to be less than the peripheral linear speed of the rollers E and F of the bonder roller arrangement, causing the material 16 to be tensioned in the machine direction and necked-in in the cross direction between the rollers B and C of the S-roll arrangement and rollers E and F of the bonder roll arrangement. By adjusting the difference in speeds of the rollers, the material 16 is tensioned so that it necks a desired amount and is maintained in such tensioned, necked condition while the elastomeric sheets 18 and 20 are attached to the material 16 during their passage through the bonder rollers F and E to form the composite material 10 having composite elastomeric necked bonded laminate strips 14 bordering a center non-extensible strip 12.

The bonder roller arrangement may include a smooth calender roller F and a smooth anvil roller E, or may include a patterned calender roller, such as a pin embossing roller, arranged with a smooth anvil roller. One or both of the calender roller and the smooth anvil roller may be heated and the pressure between these two rollers may be adjusted by well-known means to provide the desired temperature and bonding pressure to join the material 16 to the elastomeric sheets 18 and 20. Alternately, the elastomeric sheets 18, 20 may be attached to the necked material 16 by use of an adhesive, for example an elastomeric adhesive, as in known in the art.

In an alternate embodiment, the material 16 is necked prior to being joined to the sheets 18 and 20. For example, the material 16 may be supplied as a necked material directly from a supply, such as a roll.

The invention is not limited to tensioning the material 16 in the machine direction. Also, other methods of tensioning the material 16 are contemplated. For example, tenter frames or other cross-machine direction stretcher arrangements that expand the neckable material 16 in other directions, such as the cross-machine direction, may be used such that after bonding to the elastomeric sheets 18 and 20, the resulting elastomeric composite strips 14 are elastic in a direction generally perpendicular to the direction of stretching.

The necked material 16 and elastomeric sheets 18 and 20 may be completely bonded together and still provide composite elastomeric neck bonded strips 14 with good stretch properties. Alternatively, a bonding pattern, such as a sinusoidal bonding pattern, may be used.

The necked material 16 may be attached to the elastomeric sheets 18 and 20 at least at two places by any suitable means such as, for example, thermal bonding or ultrasonic welding. Joining may be produced by applying heat and/or pressure to the overlaid elastomeric sheets 18 and 20 and the necked material 16 by heating the overlaid portions to at least the softening temperature of the material with the lowest softening temperature to form a reasonably strong and permanent bond between the re-solidified softened portions of the sheets 18 and 20 and material 16. For a given combination of materials, the processing conditions necessary to achieve a satisfactory bonding can be readily determined by one of skill in the art.

The relation between the original dimensions of the neckable material 16 to its dimensions after tensioning determine the approximate limits of stretch of the composite strips 14.

Figure 2A:
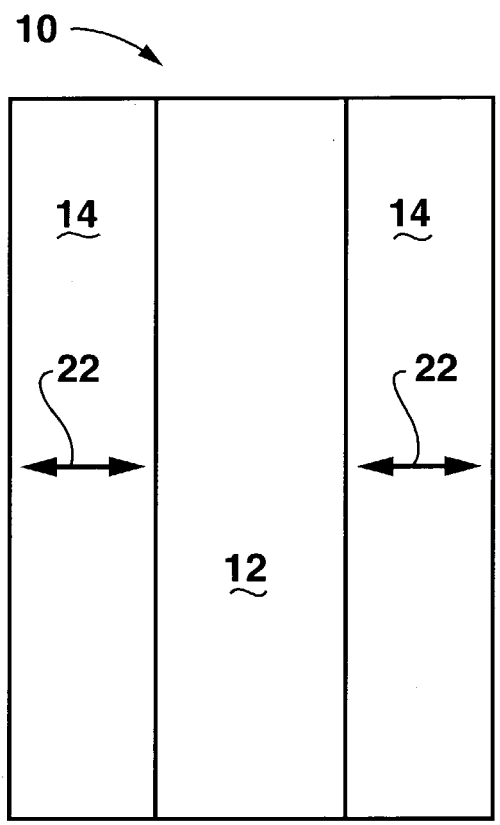
FIGS. 2A, 2B, 2C, and 2D are simplified plan views of exemplary composite material in accordance with the invention.

For example, referring to FIG. 2A wherein the composite strips 14 are stretchable in the cross-machine direction 22, if the strips have a width of, for example, 10 cm and it is desired that each of the strips 14 be stretchable to 150% of their width (i.e., to 15 cm), then the original width of the underlying material 16 along the strips 14 is at least 15 cm. As should readily be understood, the elastic limit of the sheets 18 and 20 need only be as great as the maximum desired elastic limit of the composite strips 14. In other words, the elastics sheets should be able to take the necked material back to its non-necked state.

It should be understood that the process described above with respect to FIG. 1 is presented for illustrative purposes only. Other conventional methods and machinery may be readily employed to produce a composite material 10 according to the invention. For example, a tensioned wind-up process may be used to join a necked material 16 and pressure sensitive elastomeric adhesive web of meltblown fibers 18 and 20. In an alternate embodiment, an elastomeric web sheet may be meltblown directly onto the material 16 in the regions corresponding to the composite strips 14. An additional elastomeric material may be overlaid on the meltblown sheet.

It should also be understood that the composite strips 14 and intermediate strip 12 are not limited to any particular number of material layers. For example, the underlying material 16 may include various combinations of woven or non-woven layers to achieve desired characteristics of the final composite material 10 depending on the particular end use of the material. Likewise, the elastomeric sheets 18 and 20 may include various combinations of materials to provide the strips 14 with desired characteristics.

Figure 1A:
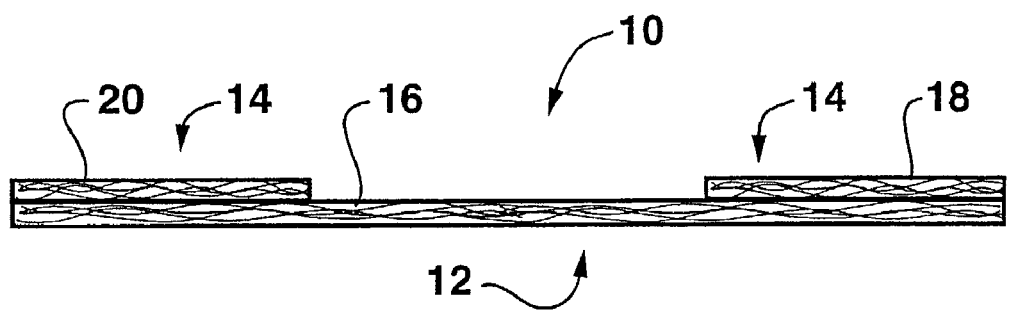
FIG. 1A is a cross-sectional schematic view of the material taken along the lines indicated in FIG. 1.
Figure 2B:
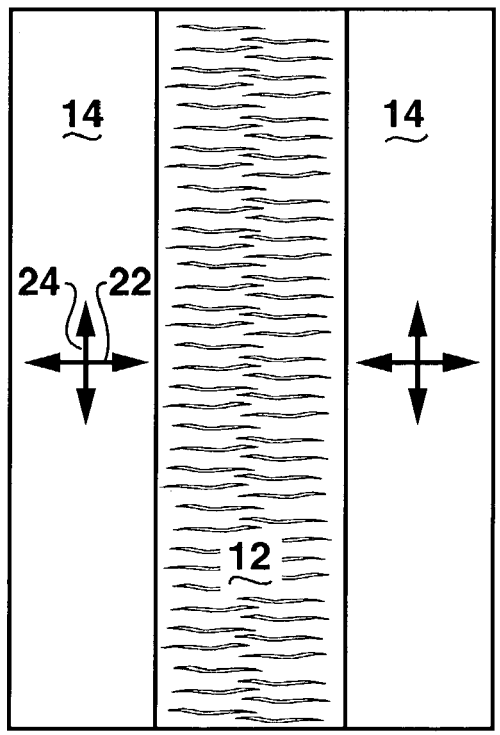

Referring to FIG. 2A, it can be seen that the material 10 includes the strip 12 of generally non-extensible material bordered on lateral sides by the composite strips 14. The strips 14 are stretchable in the transverse cross-direction 22. This embodiment may be formed, for example, by joining the elastomeric material sheets 18 and 20 in an untensioned state to the necked material 16 (FIGS. 1 and 1A). The center portion is allowed to return to its un-necked dimension (width) upon release of the necking tension. As a result, one of ordinary skill in the art can readily appreciate that the center portion of the necked material, that has returned to generally its pre-necked width, is inherently less extensible than the composite regions in a lateral direction of the necked material within the composite regions. In an alternate embodiment as depicted in FIG. 2B, the strips 14 are stretchable in the cross-direction 22 and the machine direction 24. This embodiment may be formed, for example, by attaching the elastomeric strips 18 and 20 in a tensioned state to the necked material 16. In this way, upon releasing the tensioning force on the necked material 16 and the elastomeric strips 18 and 20, the composite strips 14 essentially become necked stretch-bonded laminates that are stretchable in the machine direction and cross-direction 24, 22, and the center strip 12 is caused to gather and is extendable in the machine direction 24. On the other hand, if the center strip 12 is attached to the absorbent structure when the elastic strips 14 are still stretched, gathering of the center strip 12 will not occur and the desired capillary structure of strip 12 is retained.

In an alternate embodiment, the underlying material 16 may be mechanically processed, for example by creping, prior to attachment of the elastic strips. With this embodiment, the composite material 10 would be stretchable in the machine and cross-directions.

Figure 2C:
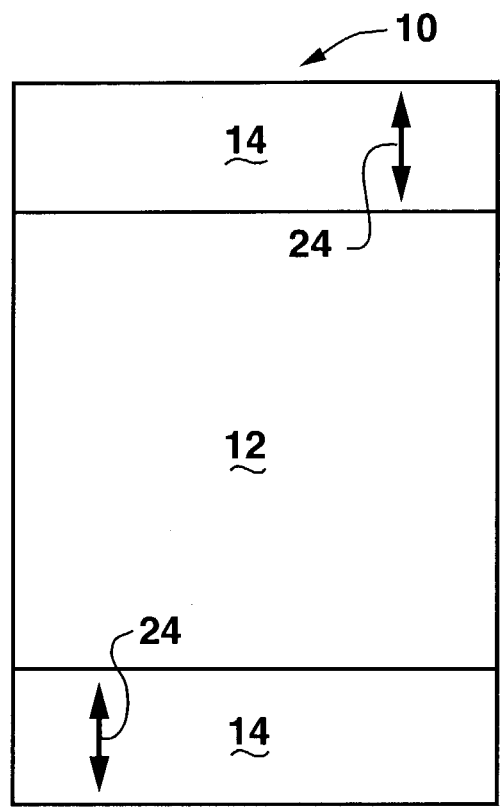

In an alternate embodiment depicted in FIG. 2C, the underlying material 16 may be tensioned in the cross direction such as by a tenter frame or other method, which may cause the material to neck-in in the machine direction. The elastomeric sheets 18 and 20 may then be attached transversely along the longitudinal ends of the material 16 such that the composite strips 14 would be oriented in the cross direction and border a center cross-direction strip 12. In this embodiment, the composite strips 14 are extensible in the machine direction 24, as shown in FIG. 2C.

Figure 2D:
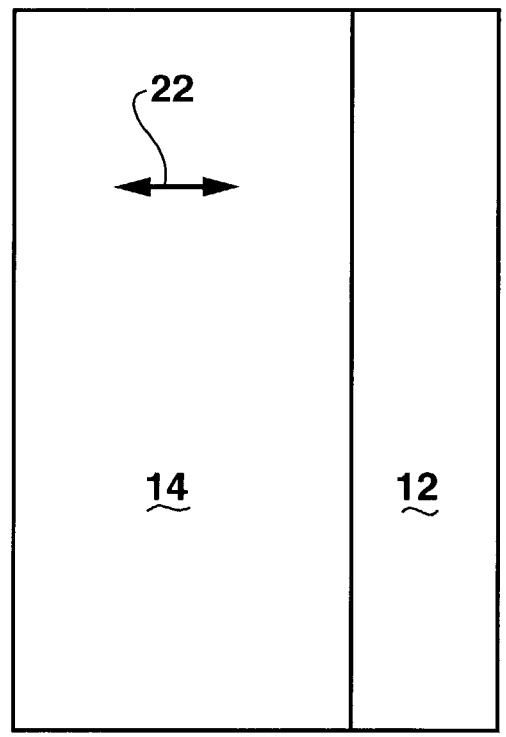

In the embodiment of FIG. 2D, a single composite strip 14 borders a lateral side of a non-extensible region 12. As described in greater detail below, the material 10 of this embodiment may be uses in various article configurations, for example the article configurations of FIGS. 7, 8, and 9.

In still another embodiment (not shown), it may be desired to completely border or "frame" the non-extensible region 12 with composite strips 14. This configuration would tend to "set" or hold the necked state of the material 16 in the region 12 such that it has a greater bulk weight. This may prove desirable in that the region 12 may function as a surge layer when overlying an absorbent body structure, such a surge layer designed primarily to receive, temporarily store, and/or transport liquid along a mutually facing surface with an absorbent structure, thereby maximizing the absorbent capacity of the absorbent structure. In one embodiment of the "framed" configuration, the composite strips 14 may be stretchable in the machine and cross directions. Alternate methods may be used to maintain the necked state of the region 12.

The non-extensible material 16 may be any one or a combination of suitable materials that are capable of being necked-in and attached with an elastomeric material. The non-extensible material 16 may be, for example, any conventional liquid permeable material used as an "inner cover" or bodyside liner of a disposable diaper, training pant, incontinence article, and the like. The material may be a non-porous material that has been perforated to render it breathable. In this regard, the material presents a body-facing surface which is compliant, softfeeling, and non-irritating to the wearer's skin. Further, the material 16 may be less hydrophilic than an underlying absorbent body of the respective absorbent article, and sufficiently porous to be liquid permeable, permitting liquid to readily penetrate through its thickness to reach the absorbent body. A suitable non-extensible material may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

Various woven and nonwoven fabrics can be used as the non-extensible material 16. For example, the material may include a meltblown web, a spunbonded web, or a bonded-carded-web composed of synthetic continuous or discrete polymer fibers and/or natural fibers, a pattern bonded spunbonded web, airlaid web, or bonded carded web, as well as combinations thereof. The various fabrics can be composed of natural fibers, synthetic fibers or combinations thereof. In particular aspects, the material may be comprised of polymer fibers, networks, laminates, liquid permeable films, cellulosic fibers, rayon, water swellable gels, as well as combinations thereof. Suitable polymers can include polypropylene, polyethylene, polyester, and bicomponent materials composed of these polyolefins.

The non-extensible material 16 may be composed of a substantially hydrophobic material, and the hydrophobic material may optionally be treated with a surfactant or otherwise processed to impart a desired level of wettability and hydrophilicity. In a particular embodiment of the invention, the material can be a nonwoven, spunbond polypropylene fabric. The fabric can be surface treated with an operative amount of surfactant, such as about 0.6% AHCOVEL Base N62 surfactant, available from ICI Americas, a business having offices located in New Castle, Del. The surfactant can be applied by any conventional means, such as spraying, dipping, printing, brush coating or the like. The fibers forming the nonwoven material may be mono-component, bi-component, or multi-component fibers, and combinations thereof.

The non-extensible material 16 may include blends or laminates of fibers, scrim, webs, and films with perforations, apertures, creping, heat activation, embossing, micro-straining, chemical treatment, or the like, as well as combinations thereof.

The elastomeric materials 18 and 20 may be any one or combination of materials that are capable of being attached to the necked non-extensible material to provide a desired degree of stretch to the resulting fabric. Depending on the end use of the material, the elastomeric materials 18 and 20 may be breathable and liquid impermeable or liquid resistant. Generally, any suitable elastomeric fiber forming resin or resin blend may be utilized for nonwoven webs of elastomeric fibers suitable for use as the elastomeric material strips. Likewise, any suitable elastomeric film forming resin or resin blend may be utilized for elastomeric films suitable for use as the elastomeric material strips. Suitable elastomeric materials can include elastic strands, Lycra® elastics, elastic films, nonwoven elastic webs, meltblown or spunbond elastomeric fibrous webs, as well as combinations thereof. Examples of elastomeric materials include Estane® elastomeric polyurethanes (available from B.F. Goodrich and Company located in Cleveland, Ohio), Pebax® elastomers (available from AtoChem located in Philadelphia, Pa.), Hytrel® elastomeric polyester (available from E. I. DuPont de Nemours located in Wilmington, Del.), Kraton® elastomer (available from Shell Chemical Company located in Houston, Tex.), strands of Lycra® elastomer (available from E. I. DuPont de Nemours located in Wilmington, Del.), or the like, as well as combinations thereof.

The elastomeric materials 18 and 20 may be a pressure sensitive elastomer adhesive sheet. For example, the elastomeric material itself may be tacky or, alternatively, a compatible tackifying resin may be added to the extrudable elastomeric compositions described above to provide an elastomeric sheet that can act as a pressure sensitive adhesive, e.g., to bond the elastomeric sheet to a tensioned, necked non-extensible material. In regard to the tackifying resins and tackified extrudable elastomeric compositions, reference is made to the resins and compositions described in U.S. Pat. No. 4,789,699, incorporated herein by reference in its entirety for all purposes.

Any tackifier resin can be used which is compatible with the elastomeric polymer and can withstand the high processing (e.g., extrusion) temperatures. If blending materials such as, for example, polyolefins or extending oils are used, the tackifier resin should also be compatible with those blending materials. Generally, hydrogenated hydrocarbon resins are preferred tackifying resins because of their better stability.

The elastomeric materials 18 and 20 may also be a multi-layer material of, for example, two or more individual coherent webs or films. Additionally, the sheets may be a multilayer material in which one or more of the layers contain a mixture of elastic and non-extensible fibers or particulates. An example of this type of material is described in U.S. Pat. No. 4,209,563, incorporated herein in its entirety by reference for all purposes, in which elastomeric and non-elastomeric fibers are commingled to form a single coherent web of randomly dispersed fibers. Another example of such a composite web is disclosed in U.S. Pat. No. 4,100,324, also incorporated herein by reference for all purposes.

As described, the composite material 10 may be incorporated for use in a wide variety of absorbent articles, such as disposable diapers, child's training pants, incontinence articles, feminine care products, and the like. The material is particularly suited for use as a bodyside liner material. Exemplary embodiments of absorbent articles will be generally described herein. However, it should be appreciated that the invention is not limited to the described embodiments. The construction and materials used in conventional absorbent articles vary widely and are well known to those of skill in the art. A detailed explanation of every such material and construction is not necessary for purposes of describing the present invention.

Figure 3:
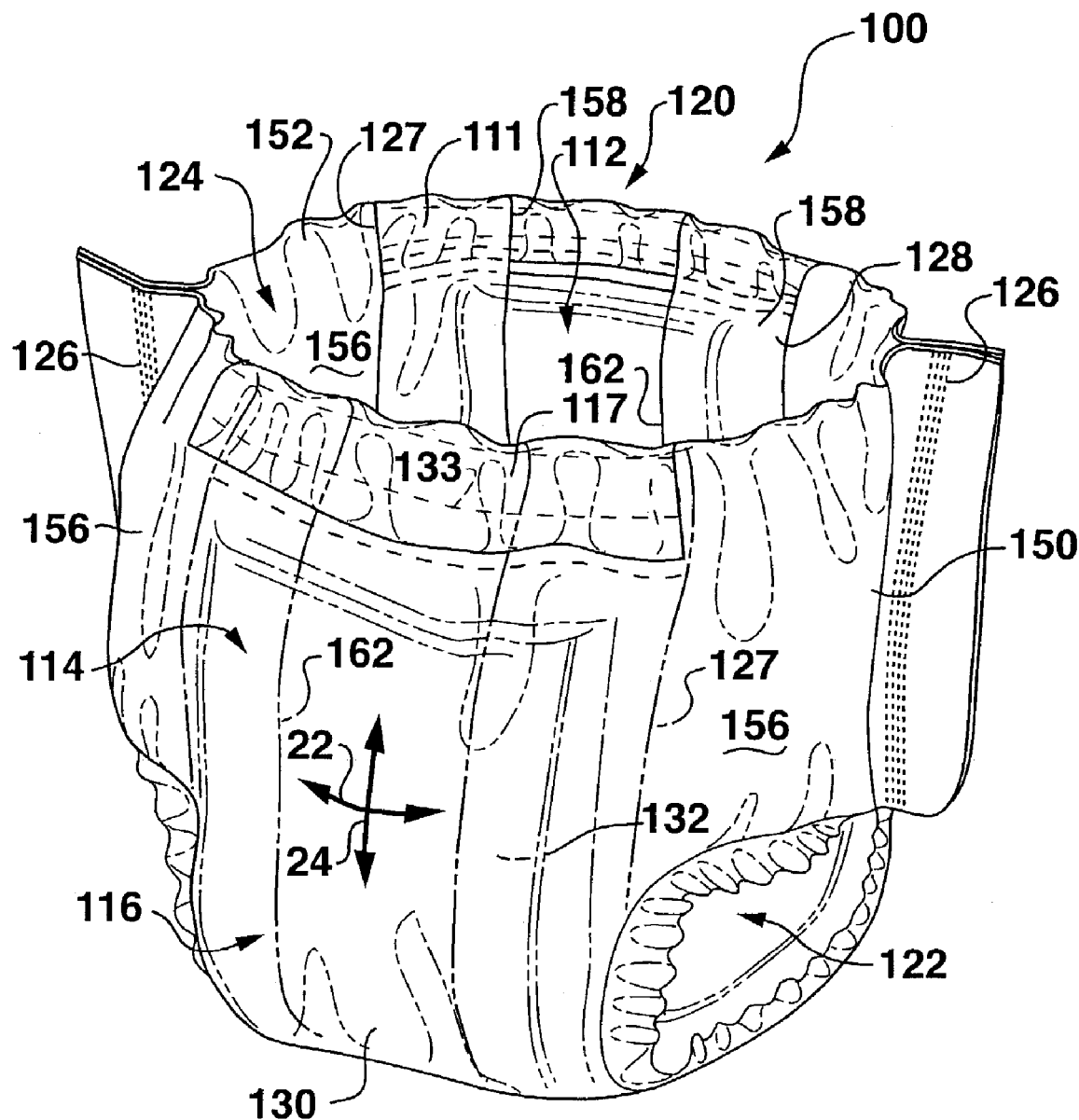
FIG. 3 is a perspective view of an absorbent article that may incorporate the composite material of the invention.

With reference to FIG. 3 in general, an article, such as the representatively shown child's training pant 100, is illustrated. This pant 100 is similar in construction and materials to the Huggies® Pull-Ups ® disposable training pants from Kimberly-Clark Corp. The article 100 includes a body or chassis 120 having a lengthwise, longitudinal direction 24, a lateral, transverse direction 22, a front waist region 114, a back waist region 112, and an intermediate crotch region 116 interconnecting the front and back waist regions. The waist regions 112 and 114 comprise those portions of the article 100 which when worn, wholly or partially cover or encircle the waist or mid-lower torso of the wearer. In particular configurations, the front 114 and back 112 waist regions may include elastic front and back waistband portions 117, 111 incorporating elastic members 133. In the embodiment of FIG. 3, the elastic waistband portions 111,117 extend only partially across their respective waist regions. In an alternate embodiment, the waistband portions 117, 111 may be generally continuous around the waist opening of the article. The intermediate crotch region 116 lies between and interconnects the waist regions 114 and 112, and comprises that portion of the article 100 which, when worn, is positioned between the legs of the wearer and covers the lower torso of the wearer. Thus, the intermediate crotch region 116 is an area where repeated fluid surges typically occur in the training pant or other disposable absorbent article.

The article 100 includes a substantially liquid-impermeable outer cover member 130, a liquid-permeable bodyside liner 128, and an absorbent body structure 132 sandwiched between the outer cover member 130 and the bodyside liner layer 128. The absorbent body structure may be secured to the outer cover member 130 by an adhesive. The adhesive may be applied along the centerline of the absorbent structure in the case of a lateral/transverse stretch outer cover, or in a transverse line in the case of a longitudinal stretch outer cover, on in a spot pattern in the case of a lateral and longitudinal stretch outer cover.

For various reasons such as product comfort, performance, size range, etc., it is generally known that particular portions and components of the chassis 120 may be formed of elastomeric materials and thus be stretchable, particularly in the lateral or transverse direction 22. In the illustrated embodiment of the article 100, the chassis 120 includes stretchable front side panel portions 150 and back side panel portions 152 laterally extending from the central structure of the chassis 120.

This configuration is common for training pants and provides the article with a desired degree of stretchability in the transverse direction 22 across the waist regions 112, 114. With a known conventional arrangement as depicted in FIG. 3, the panel portions 150, 152 are defined by generally elastomeric side panels 156 that are attached to the lateral sides of the chassis 120 at the waist regions 112, 114, for example along adhesive seam lines 127.

In an alternate embodiment, the separate panel portions 150, 152 may not be needed, and may be defined by an extension of the chassis 120, for example, extensions of the outer cover member 130, bodyside liner 128, or both. The composite material 10 of the present invention is particularly well suited for this configuration, as explained in greater detail below with reference to FIGS. 4A, 5, and 6. For example, the chassis may include an elastomeric cover member 130, elastomeric bodyside liner 128, and any combination of other elastomeric components that in combination render a stretchable unitary chassis that does not compromise the structural integrity and absorbency of the absorbent article 132.

The training pant embodiment 100 may be of a style and configuration wherein the front and back ear portions 150, 152 have lateral sides that are brought together upon folding the chassis to form a pant-like structure having the waist opening 124 and leg openings 122. The lateral sides are bonded in a known manner so as to define side seams 126 (FIG. 3) of the pant structure. With this type of configuration, the pant 100 is pulled on by the wearer in a manner similar to underwear. Desirably, these seams 126 may be separable or tearable so that the pant 100 may be removed from the wearer by tearing the seams 126 and removing the article in a manner similar to a diaper. In an alternate embodiment, the front and back panel portions 150, 152 may be separable and re-attachable at the side seams 126. A fastening system, such as a hook-and-loop system, may be used to interconnect the first waist region 112 with the second waist region 114 to define the pant structure and hold the article on a wearer. Additional suitable releasable fastening systems are described in U.S. Pat. No. 6,231,557 B1 and the International Application WO 00/35395, these references being incorporated herein by reference in their entirety for all purposes.

Figure 4:
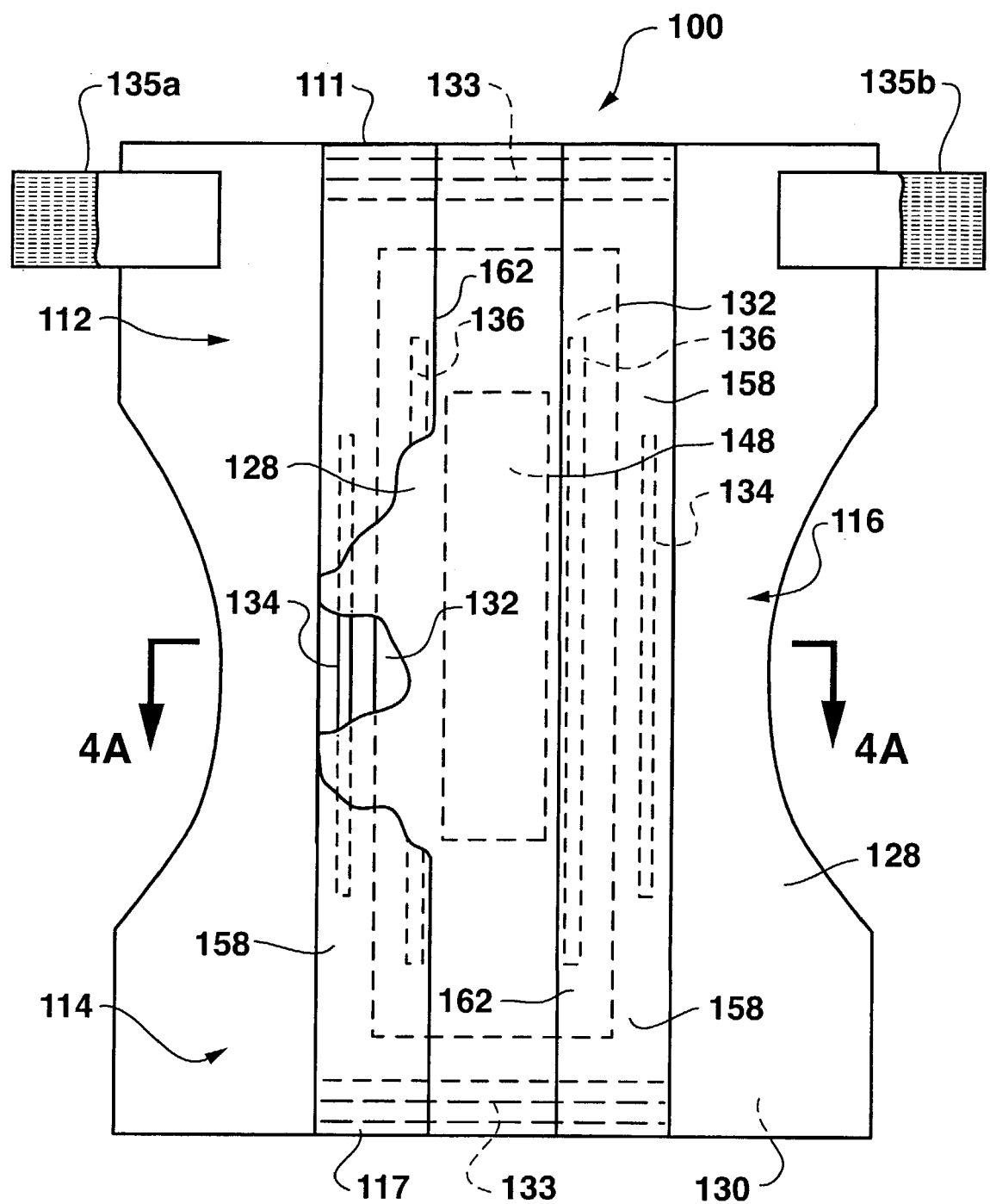
FIG. 4 is a plan view in partial cutaway of an absorbent article that may incorporate the composite material of the invention.

An article 100 according to the invention may also incorporate longitudinally extending containment flaps 158 disposed over the bodyside liner 128, as generally understood in the art and shown in FIGS. 3, 4, and 4A. The flaps 158 have longitudinal ends that are attached to the chassis 120 generally at the waistband portions 117, 111. In certain embodiments of the invention, the flaps 158 may comprise separate panels or sheets of material having an outboard lateral side that is attached to the chassis 120 desirably outboard of the underlying absorbent body structure 132. Referring to FIG. 3, the flaps 158 may be attached, for example, along the seam line 127. In an alternate embodiment, the flaps 158 may be defined by a folded configuration of the bodyside liner 128, as described in greater detail below. The flaps 158 have a laterally inboard "free" side 162 such that the guards essentially define a containment pocket along the lateral sides of the absorbent structure 132. The free sides 162 may incorporate flap elastics 136 along their longitudinal side, as is generally known in the art.

FIG. 4 shows a body facing plan view of a representative article 100, in this case a disposable diaper, in its generally flat-out, uncontracted state (i.e., with substantially all elastic induced gathering and contraction removed). The diaper incorporates any manner of conventional securing or fastening device, such as hook or loop tabs 135a and 135b as illustrated. The tabs 135a and 135b may engage directly with the outer cover member or with corresponding loop or hook material provided on the outer cover member 130, as in known in the art. The components are attached or joined together by conventional suitable attachment methods such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the various components.

The diaper 100 will typically include a porous, liquid permeable bodyside liner 128 overlying an absorbent body structure 132; a substantially liquid impermeable outer cover member 130; and the absorbent body structure 132 positioned and attached between the outer cover member 130 and bodyside liner 128. In certain embodiments, a surge layer 148 may be optionally located adjacent the absorbent structure and attached, for example, by way of an adhesive.

As depicted in FIG. 4a, the outer cover member 130 and bodyside liner 128 may be separate sheets joined at their respective lateral sides. Leg elastics 134 may be incorporated along the lateral side margins of the chassis 120 outboard of the absorbent body structure 132 and are configured to draw and hold the chassis 120 against the legs of the wearer. The liner 128, outer cover 130, absorbent structure 132, surge layer 148, and elastic members 134 and 132 may be assembled together into a variety of well-known absorbent article configurations.

The elastic members 134 are secured to the chassis 120 in an elastically contracted state so that in a normal under-strain condition, the elastic members 134 effectively contract against the wearer's body. The use of elastic leg members in absorbent articles such as disposable diapers and training pants is widely known and understood in the art.

The use of elastic waistbands is also widely known and used in the art. In the illustrated embodiments of FIGS. 3 and 4, the waist elastics 133 are provided only partially across the front and back waistbands 117, 111. The waist elastics 133 may be composed of any suitable elastomeric material, such as an elastomeric film, an elastic foam, multiple elastic strands, an elastomeric fabric, and the like. Embodiments of waistband structures that may be utilized with articles 100 according to the invention are also described in U.S. Pat. Nos. 5,601,547; 5,500,063; 5,545,158; 6,358,350 B1; 6,336,921 B1; and 5,711,832, incorporated by reference in their entirety for all purposes.

In certain embodiments utilizing the composite material 10 according to the invention, the composite elastomeric strips 14 may provide sufficient stretch properties to the chassis in the transverse direction such that separately applied elasticized waistband structures may be eliminated.

FIG. 4A is a schematic cross-sectional view of a disposable diaper 100 taken along the lines indicated in FIG. 4. In this embodiment, the bodyside liner 128 is composed of the material 10 described above. In FIG. 4A (as well as FIGS. 5 and 6), the composite portions 14 of the material are shown with slight crosshatching to represent that these portions are a multi-layer/composite elastic structure. The material may be formed off-line and incorporated directly into the in-line manufacturing process of the absorbent article 100. Alternately, the material may be formed and conveyed directly into the in-line manufacturing of the articles 100. The base material 16 (FIG. 1) of the composite material is generally liquid permeable and may be any material suited for use as a bodyside liner. The strip or region 12 of the composite material 10 is non-extensible and is disposed over the absorbent body structure 132. A surge layer 148 may be placed between the absorbent structure 132 and non-extensible strip 12. It may be desired to adhere the entire overlying portion of the strip 12 to the absorbent structure 132 (or surge layer 148) with an adhesive 183. With this configuration, the capillary structure of the overlying region of the strip 12 is maintained even with transverse stretching of the composite strips 14. The composite elastomeric side strips or regions 14 extend laterally outward from the center strip 12 to the lateral sides of the chassis 120 and are joined to the outer cover member 130 for example by thermal bonding and/or adhesive 185. The outer cover member 130 may be adhered to the absorbent body structure 132 with a centerline adhesive 182. As mentioned, leg elastics 134 may be incorporated along the lateral seams between the outer cover member 130 and composite strips 14. In this configuration, the composite strips 14 provide a transverse stretchability to the bodyside liner 128 without the need to attach separate side panels or materials to side edges of a suitable bodyside liner material. The composite strips 14 will stretch in the transverse direction without imparting distorting tension to the non-extensible center strip 12 and underlying absorbent body structure 132. In this embodiment, it may be desired that the outer cover member 130 is also elastomeric.

Various materials are available and known in the art for use as separate outer cover members 130. Constructions of the outer cover member 130 may comprise a woven or nonwoven fibrous web layer which has been totally or partially constructed or treated to impart the desired levels of liquid impermeability to selected regions that are adjacent or proximate the absorbent body. Alternatively, a separate liquid impermeable material could be associated with the absorbent body structure 132. The outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material. Although the outer cover member 130 typically provides the outermost layer of the article, optionally the article may include a separate outer cover component member which is additional to the outer cover member.

As mentioned, the outer cover member 130 may be formed substantially from an elastomeric material. Alternately, the outer cover member may be formed from an extendable material that is non-elastomeric. The outer cover member 130 may, for example, be composed of a single layer, multiple layers, laminates, spunbond fabrics, films, meltblown fabrics, elastic netting, microporous web, bonded carded webs or foams comprised of elastomeric or polymeric materials. Elastomeric nonwoven laminate webs may include a nonwoven material joined to one or more gatherable nonwoven webs, films, or foams. Stretch Bonded Laminates (SBL), Neck Bonded Laminates (NBL), and Necked Stretch Bonded Laminates (NSBL) are examples of elastomeric composites. Nonwoven fabrics are any web of material which has been formed without the use of textile weaving processes which produce a structure of individual fibers which are interwoven in an identifiable repeating manner. Examples of suitable materials are Spunbond-Meltblown fabrics, Spunbond-Meltblown-Spunbond fabrics, Spunbond fabrics, or laminates of such fabrics with films, foams, or other nonwoven webs. Elastomeric materials may include cast or blown films, foams, or meltblown fabrics composed of polyethylene, polypropylene, or polyolefin copolymers, as well as combinations thereof. The outer cover 130 may include materials that have elastomeric or extensible properties obtained through a mechanical process, printing process, heating process, or chemical treatment. For example such materials may be apertured, creped, neck-stretched, heat activated, embossed, and micro-strained; and may be in the form of films, webs, and laminates.

As illustrated in FIG. 4A, the article 100 may incorporate separate containment flaps 158 attached to the sides of the composite material, for example to the elastomeric strips 14. The flaps 158 may contain elastic members 136 along at least a portion of their free laterally inward side 162. The construction of such containment flaps 158 is well known and need not be described in detail. Suitable constructions and arrangements for the containment flaps 158 are described, for example, in U.S. Pat. No. 4,704,116, which is incorporated herein by reference for all purposes.

An alternate embodiment of an absorbent article 100 according to the invention is illustrated in FIG. 4B, which is similar in many respects to the embodiment of FIG. 4A. With this embodiment, however, the elastomeric strips 14 have a sufficient width so as to wrap around the absorbent body structure 132 and attach to each other at some location generally "under" the absorbent body structure. Thus, the strips 14 essentially encase the absorbent body structure 132 and define the outer cover 130. The non-extensible region 12 overlying the surge layer 148 is adhered generally entirely to the surge layer with an adhesive 183 such that the capillary structure of the region 12 is "set" and will generally not be affected by stretching of the side strips 14. The strips 14 are attached to the underside of the absorbent body structure 132 by a centerline strip of adhesive 182. With this configuration, the strips 14 define elastomeric portions of the bodyside liner 128 and an elastomeric outer cover 130. Side panels 156 (elastic or non-extensible) may be attached to the strips 14 at the lateral sides of the chassis.

Figure 7:
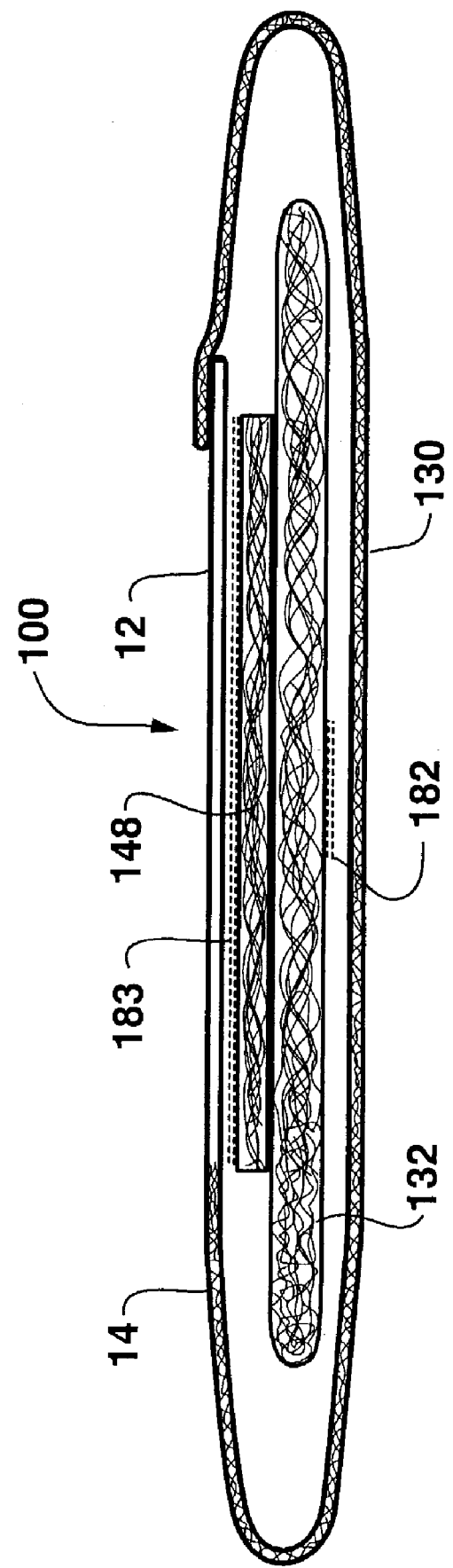
FIG. 7 is a schematic cross-sectional view of an alternate embodiment of an absorbent article according to the invention.

FIG. 7 illustrates an embodiment that is similar to the embodiment of FIG. 4B with the exception that a material 10 as illustrated in FIG. 2D is used. Here, the single composite side strip 14 has a sufficient width so as to fold under the absorbent body structure 132 and attach to the opposite lateral side of the region 12 of non-extensible material. Thus, the single composite side strip 14 also defines the outer cover member 130.

FIG. 5 illustrates another embodiment of an absorbent article 100 incorporating the composite material 10. The embodiment of FIG. 5 is similar in many respects to that of FIG. 4B. This embodiment may be, for example, a training pant incorporating elastomeric side panels 156 as described above with respect to FIG. 3. The non-extensible strip 12 has a sufficient width so as to overlie the surge layer 148 (or absorbent body structure 132 if a surge layer is not provided) and is attached to the surge layer 148 with an adhesive 183, as discussed above with respect to FIGS. 4A and 4B. With this embodiment, the elastomeric side strips may be formed by two different materials 14a and 14b. For example, material 14a may include a breathable liquid impervious film, or a liquid permeable elastomeric nonwoven material. Additional strips 14b may be attached to the strips 14a, for example at the lateral side folds 129, and include a breathable liquid impervious material.

It should be appreciated that different elastomeric properties/regions in the strips 14 can be achieved in other ways as well. Examples include two different materials disposed side-by-side (with or without partial overlap), two different materials overlapping, or a type of post treatment of part of an elastomeric layer, such as post-bonding a smaller region to generate different elastomeric properties in that sub-region.

Referring to FIG. 1, the composite material used in this embodiment may be formed by attaching two different strips of elastomeric material to each side of the non-extensible center region 12. In other words, the strip 18 would be defined by adjacent strips 18a and 18b (not shown), and strip 20 would be defined by adjacent strips 20a and 20b. The edges of the strips 14*b* are attached together and to the absorbent body structure 132, for example with a centerline adhesive 182. The leg elastics 134 are provided in the folded lateral margins and elastomeric side panels 156 may be attached along the lateral margins at bond lines 127. Thus, with this embodiment, the material 10 defines the bodyside liner 128 and the outer cover member 130, and provides desirable elastomeric stretch properties to these components.

The base material 16 of the composite material 10 would be selected in this embodiment to provide the desired characteristics of a bodyside liner, whereas the elastomeric materials 18 and 20 would be selected to provide the desired characteristics of an outer cover member 130.

As illustrated in FIG. 5, the containment flaps 158 may be defined by folded portions of the elastomeric strips 14*a*. For example, the strips may be folded in a Z-configuration as illustrated and incorporate the flap elastic members 136 in the folded layers. A suitable adhesive may be used to attach the elastic member 136 and "set" the folded configuration. Alternatively, separate containment flaps may be incorporated as in the embodiment of FIG. 4A.

The elastomeric side panels may be permanently bonded to the lateral sides of the chassis 120 at bond lines 127 using attachment means known to those skilled in the art, such as adhesive, thermal or ultrasonic bonding. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753, which is incorporated by reference herein in its entirety for all purposes. The lateral outboard sides of the side panels 156 may then be permanently or releasably attached along side seams 126 to define a pant structure. These bonded side seams may be tearable as discussed above. Alternately, the side panels may be releasably attachable along the side seams 126 using any type of suitable releasable fastener system, as discussed above.

Suitable elastic materials for the side panels 156, as well as a described process of incorporating elastic side panels into a training pant, are described, for example, in the following U.S. Pat. Nos.: 4,940,464; 5,224,405; 5,104,116; 5,046,272; and WO 01/88245 all of which are incorporated herein by reference in their entirety for all purposes. In particular embodiments, the elastic material comprises a stretch-thermal laminate (STL), a neck-bonded laminate (NBL), a reversibly necked laminate, or a stretch-bonded laminate (SBL) material. Methods of making such materials are described, for example, in U.S. Pat. Nos. 4,663,220; 5,226,992; and the EP Application 0 217 032, all of which are incorporated herein by reference in their entirety for all purposes.

The article 100 of FIG. 6 is an alternate embodiment similar in many respects to the embodiment of FIG. 5. However, in this embodiment, the composite elastomeric strips 14 are substantially wider and also define the elastomeric side panels 156. This configuration may be particularly desirable for training pants in that a single sheet of material is used to define the bodyside liner 128, outer cover member 130, and stretchable side panels 156. The training pant article 100 would have desired stretchability across the waist and side regions of the wearer and have an overall underwear like appearance. Substantially fewer materials would be used and the complexity of the manufacturing process would be significantly reduced.

The embodiment of FIG. 8 is similar in many respects to that of FIG. 5 with the exception that the material 10 is FIG. 2D is used. In this embodiment, the single composite strip 14 has a sufficient width and is folded so as to define the containment flaps 158 and the outer cover 130. The strip 14 is attached by any suitable means to the opposite lateral side of the region 12 of non-extensible material overlying the absorbent body structure 132.

Likewise, the embodiment of FIG. 9 is similar to the embodiment of FIG. 6 with the exception that the material 10 of FIG. 2*d* is used. In this embodiment, the single composite strip 14 has a sufficient width and is folded so as to define the elastomeric side panels 156, containment flaps 158, and outer cover 130. The strip is attached by any suitable means to the opposite lateral side of the region 12 of non-extensible material overlying the absorbent body structure. 132.

The absorbent body structure 132 can be any structure or combination of components which are generally compressible, conformable, non-irritating to a wearer's skin, and capable of absorbing and retaining liquids and certain body wastes. For example, the structure 132 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from U.S. Alliance of Childersburg, Ala., USA, and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

As a general rule, the superabsorbent material is present in the absorbent web in an amount of from about 0 to about 90 weight percent based on total weight of the web. The web may have a density within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and desirably is capable of absorbing more than about 25 times its weight in liquid. Suitable superabsorbent materials are readily available from various suppliers. For example, Favor 880 superabsorbent is available from Stockhausen GmbH of Germany; and Drytech 2035 is available from Dow Chemical Company, of Midland Mich., USA.

After being formed or cut into a desired shape, the absorbent web material may be wrapped or encompassed by a suitable wrap that aids in maintaining the integrity and shape of the absorbent structure 132.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. Nos. 4,100,324 to Anderson, et al.; 5,284,703 to Everhart, et al.; and 5,350,624 to Georger, et al.; which are incorporated herein in their entirety by reference thereto for all purposes.

The absorbent body structure 32 may include an elastomeric coform absorbent web material, for example as described in U.S. Pat. Nos. 4,663,220 and 4,741,949. In particular aspects, the elastomeric coform material can have an overall coform basis weight which is at least a minimum of about 50 g/m$^2$. The coform basis weight can alternatively be at least about 100 g/m$^2$ and can optionally be at least about 200 gIm$^2$ to provide improved performance. In addition, the coform basis weight can be not more than about 1200 g/m$^2$. Alternatively, the coform basis weight can be not more than about 900 g/m$^2$, and optionally, can be not more than about 800 g/m$^2$ to provide improved benefits. These values are important because they can provide the absorbent body structure with desired stretchability and structural stability without excessively degrading the physical properties or the liquid-management functionalities of the absorbent body structure. Retention portions having excessively low proportions of elastomeric coform material may not be sufficiently stretchable. An absorbent web material having excessively large amounts of elastomeric coform materials can exhibit an excessive degradation of their absorbency functionalities, such as an excessive degradation of intake, distribution and/or retention properties.

Other examples of elastomeric absorbent structures are described in U.S. Pat. No. 6,362,389 B1, incorporated herein by reference for all purposes.

The absorbent web material utilized in the absorbent body structure 32 is also selected so that the individual absorbent body structure possesses a particular individual total absorbency depending on the intended article of use. For example, for infant care products, the total absorbency can be within the range of about 200-900 grams of 0.9 wt % saline, and can typically be about 500 g of saline. For adult care products, the total absorbency can be within the range of about 400-2000 grams of saline, and can typically be about 1300 g of saline. For feminine care products, the total absorbency can be within the range of about 7-50 grams of menstrual fluid, and can typically be within the range of about 30-40 g of menstrual fluid.

As described, the absorbent body structure 132 may also include a surge management layer 148 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. The surge layer can be located below the bodyside liner layer 128. Alternatively, the surge layer may be located on the body facing surface of the bodyside liner 128. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference in their entirety for all purposes.

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. An absorbent article, comprising:
   a chassis having a front waist region, a back waist region, and a crotch region extending between said front and back waist regions;
   an outer cover member extending longitudinally between said front and back waist regions;
   a bodyside liner extending longitudinally between said front and back waist regions;
   an absorbent body structure sandwiched between said outer cover member and said bodyside liner;
   said bodyside liner comprising a material having
      a generally non-elastic base layer of a fluid permeable material;
      first and second separate strips of elastomeric material attached to said base layer material in a necked condition of said base layer material with a space between said separate strips of elastomeric material to define composite regions of said elastomeric material and said necked base layer material, said space between said composite regions defining a center region of said base layer material that has returned to generally its pre-necked width, overlies said absorbent body structure, and is inherently less extensible than said composite regions in a lateral direction of said necked base layer material within said composite regions; and
      wherein said center region of said base layer material remains generally non-elastic and said composite regions are elastic and stretchable in at least a lateral direction in use of said absorbent article.

2. The absorbent article as in claim 1, wherein said article is a child's training pant.

3. The absorbent article as in claim 1, wherein said article is a disposable diaper.

4. The absorbent article as in claim 1, wherein said article is an incontinence article.

5. The absorbent article as in claim 1, wherein said article is a feminine hygiene article.

6. The absorbent article as in claim 1, wherein said first and second elastomeric materials are superimposed on and aligned with respective lateral sides of said underlying base layer material.

7. The absorbent article as in claim 1, wherein said base layer material comprises a non-woven material.

8. The absorbent article as in claim 7, wherein said non-woven material comprises a spunbond material.

9. The absorbent article as in claim 1, wherein said first and second elastomeric materials comprise an elastic film, said films being laminated to said base layer material such that said composite regions are neck bonded laminate regions.

10. The absorbent article as in claim 1, wherein said first and second elastomeric materials comprise webs of elastomeric fibers.

11. The absorbent article as in claim 1, wherein said base layer material is tensioned in the longitudinal direction prior to attaching said first and second elastomeric materials to opposite lateral sides of said base layer material such that said bodyside liner has longitudinal strips of said composite regions that are stretchable in the transverse direction bordering a center machine direction region of said base layer material.

12. The absorbent article as in claim 11, wherein said elastomeric materials are attached to said base layer material in a generally untensioned state.

13. The absorbent article as in claim 11, wherein said elastomeric materials are attached to said base layer material in a tensioned state.

14. The absorbent article as in claim 1, wherein said base layer material is tensioned in the cross direction, and said first and second elastomeric materials are attached in the cross direction to opposite longitudinal ends of said base layer material such that said composite regions of said bodyside liner extend generally across said front and back waist regions of said chassis.

15. The absorbent article as in claim 1, wherein said base layer material is tensioned in the machine direction, and said first and second elastomeric materials are attached to opposite lateral sides of said base layer material and attached in the cross direction to opposite longitudinal ends of said base layer material such that said composite regions of said bodyside liner extend in the longitudinal direction on each side of said center region and generally transversely across said front and back waist regions of said chassis.

16. The absorbent article as in claim 1, wherein said base layer material is tensioned in a machine direction prior to attachment of said first and second elastomeric materials to opposite lateral sides of said base layer material, said base layer material being rendered stretchable such that said bodyside liner material is stretchable in the transverse direction and the longitudinal direction.

17. The absorbent article as in claim 16, wherein said base layer material comprises a creped material.

18. The absorbent article as in claim 1, wherein said bodyside liner is a separate component from said outer cover member, said bodyside liner and said outer cover member being generally coextensive and attached along side seams of said chassis, said composite regions of said bodyside liner defining longitudinal strips on each side of said center region and extending outwardly from said center region to said respective side seams.

19. The absorbent article as in claim 18, further comprising longitudinally extending containment flaps attached to said chassis over said bodyside liner generally outboard of respective opposite lateral sides of said absorbent body structure.

20. The absorbent article as in claim 18, wherein portions of said composite regions of said bodyside liner are folded outboard of said absorbent body structure so as to define longitudinally extending containment flaps on opposite lateral sides of said absorbent body structure.

21. The absorbent article as in claim 1, wherein said composite regions of said bodyside liner define machine direction strips extending laterally from said center region, said composite strips folded at a side fold line of said chassis and extending laterally back under said absorbent body structure and attached to each other such that said composite regions also define said outer cover member of said chassis.

22. The absorbent article as in claim 21, wherein said article is a child's training pant.

23. The absorbent article as in claim 22, further comprising leg elastics incorporated in said fold lines.

24. The absorbent article as in claim 21, further comprising elastomeric side panels attached to said chassis at said fold lines, said side panels attached at side seams to define a pant-like structure.

25. The absorbent article as in claim 21, wherein portions of said composite regions of said bodyside liner are folded outboard of said absorbent body structure so as to define longitudinally extending containment flaps on opposite lateral sides of said absorbent body structure.

26. The absorbent article as in claim 25, further comprising longitudinally extending elastic components incorporated in said folded containment flaps.

27. The absorbent article as in claim 21, wherein said composite regions are also attached to an underside of said absorbent body structure.

28. The absorbent article as in claim 1, wherein said composite regions of said bodyside liner define longitudinal strips extending outwardly from said center region and defining elastomeric side panels that are attached at side seams of said chassis to define a pant-like structure, said composite strips folded outboard of said side panels at fold lines and extending laterally back under said absorbent body structure and attached to each other such that said composite regions also define said outer cover member of said chassis.

29. The absorbent article as in claim 28, wherein said article is a child's training pant.

30. The absorbent article as in claim 28, further comprising leg elastics incorporated in said side panels between said folded portions of said composite regions.

31. The absorbent article as in claim 28, wherein portions of said composite regions of said bodyside liner are folded outboard of said absorbent body structure so as to define longitudinally extending containment flaps on opposite lateral sides of said absorbent body structure.

32. The absorbent article as in claim 31, further comprising longitudinally extending elastic components incorporated in said folded containment flaps.

33. The absorbent article as in claim 28, wherein said composite regions are also attached to an underside of said absorbent body structure.

34. The absorbent article as in claim 1, wherein said composite regions of said bodyside liner define longitudinally extending strips extending laterally outward from said center region and defining elastomeric side panels that are attached at side seams of said chassis to define a pant-like structure, said composite strips folded outboard of said side panels at fold lines and extending laterally back under said absorbent body structure and attached to each other such that said composite regions also define said outer cover member of said chassis; and wherein portions of said composite regions of said bodyside liner are folded outboard of said absorbent body structure so as to define longitudinally extending containment flaps on opposite lateral sides of said absorbent body structure.

35. The absorbent article as in claim 1, wherein said composite regions of said bodyside liner define longitudinally extending strips extending laterally outward from said center region, said composite strips folded at a side fold line of said chassis and extending laterally back under said absorbent body structure and attached to each other such that said composite regions also define said outer cover member of said chassis;

wherein portions of said composite regions of said bodyside liner are folded outboard of said absorbent body structure so as to define longitudinally extending containment flaps on opposite lateral sides of said absorbent body structure; and further comprising elastomeric side panels attached to said chassis at said fold lines, said side panels attached at side seams to define a pant-like structure.

36. An absorbent article, comprising:
a chassis having a front waist region, a back waist region, and a crotch region extending between said front and back waist regions;
an outer cover member extending longitudinally between said front and back waist regions;
a bodyside liner extending longitudinally between said front and back waist regions;
an absorbent body structure sandwiched between said outer cover member and said bodyside liner;
said bodyside liner comprising a material having
a generally non-elastic base layer of a generally fluid permeable material having a necked region adjacent to a relaxed region which has returned generally to its pre-necked width;
a strip of elastomeric material attached to said necked region of said base layer material such that said relaxed region of said base layer material is adjacent at least one composite region of said elastomeric material and said necked base layer material, said relaxed region of said base layer material generally overlying said absorbent body structure without additional material disposed between said relaxed region of said base layer material and said absorbent body structure to render said relaxed region of said base layer material less extensible; and
wherein said relaxed region of said base layer material remains generally non-elastic and inherently less extensible than said composite region and said composite region is stretchable in at least a lateral direction of said base layer in use of said absorbent article.

37. The absorbent article as in claim 36, wherein said elastomeric material is superimposed on and aligned with a lateral side of said underlying base layer material.

38. The absorbent article as in claim 36, wherein said base layer material is tensioned in the longitudinal direction prior to attaching said elastomeric material to a lateral side of said base layer material such that said bodyside liner has a longitudinal strip of said composite region that is stretchable in the transverse direction adjacent said region of said base layer material.

39. The absorbent article as in claim 38, wherein said elastomeric material is attached to said base layer material in a generally untensioned state.

40. The absorbent article as in claim 38, wherein said elastomeric material is attached to said base layer material in a tensioned state.

41. The absorbent article as in claim 36, wherein said composite region of said bodyside liner is folded at a side fold line of said chassis and extends laterally back under said absorbent body structure and attaches to an opposite lateral side of said region of base layer material such that said composite region also defines said outer cover member of said chassis.

42. The absorbent article as in claim 41, wherein said composite region of said bodyside liner is folded outboard of said absorbent body structure so as to define longitudinally extending containment flaps on opposite lateral sides of said absorbent body structure.

43. The absorbent article as in claim 41, wherein said composite region of said bodyside liner is folded so as to define longitudinally extending elastomeric side panels outboard of said absorbent body structure.

* * * * *